(12) United States Patent
Sayama

(10) Patent No.: US 10,590,180 B2
(45) Date of Patent: Mar. 17, 2020

(54) IMMUNE FUNCTION DEVELOPMENT PROMOTER AND GROWTH PROMOTER

(71) Applicant: NATIONAL UNIVERSITY CORPORATION SHIZUOKA UNIVERSITY, Shizuoka-shi, Shizuoka (JP)

(72) Inventor: Kazutoshi Sayama, Shizuoka (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 0 days.

(21) Appl. No.: 15/736,961

(22) PCT Filed: Jun. 17, 2016

(86) PCT No.: PCT/JP2016/068098
§ 371 (c)(1),
(2) Date: Dec. 15, 2017

(87) PCT Pub. No.: WO2016/204271
PCT Pub. Date: Dec. 22, 2016

(65) Prior Publication Data
US 2018/0369335 A1    Dec. 27, 2018

(30) Foreign Application Priority Data
Jun. 19, 2015   (JP) ................. 2015-123682

(51) Int. Cl.
| | | |
|---|---|---|
| *A61K 38/19* | (2006.01) | |
| *C07K 14/52* | (2006.01) | |
| *A61P 37/04* | (2006.01) | |
| *A61K 9/00* | (2006.01) | |
| *A23L 33/19* | (2016.01) | |
| *A23C 23/00* | (2006.01) | |
| *A23L 33/00* | (2016.01) | |

(52) U.S. Cl.
CPC ............ *C07K 14/52* (2013.01); *A61K 9/0053* (2013.01); *A61P 37/04* (2018.01); *A23C 23/00* (2013.01); *A23L 33/19* (2016.08); *A23L 33/40* (2016.08); *A61K 9/0095* (2013.01); *A61K 38/195* (2013.01)

(58) Field of Classification Search
None
See application file for complete search history.

(56) References Cited

U.S. PATENT DOCUMENTS

2007/0009495 A1*  1/2007  McMahon ........... A61K 31/201
                                                    424/93.7

FOREIGN PATENT DOCUMENTS

| WO | WO 03/041512 A1 | 5/2003 |
| WO | WO 03/089593 A2 | 10/2003 |
| WO | WO 2014/187743 | 11/2014 |
| WO | WO 2015/079952 A1 | 6/2015 |

OTHER PUBLICATIONS

Sayama et al. https://kaken.nii.ac.jp/grant/KAKENHI-PROJECT-25560048/ (Year: 2014).*
Sayama et al. Elucidation of physiological functionality of CCL25 in milk for the enhancement of gut immunity in neonate, p. 1-12. (Google translation) (Year: 2014).*
Levast, B. et al., "Ultra-early weaning in piglets results in low serum IgA concentration and IL17 mRNA expression", Veterinary Immunology and Immunopathology,vol. 137, 2010, p. 261-p. 268.
Kathuria, N. et al., "Generation of antigen-specific immunity following systemic immunization with DNA vaccine encoding CCL25 chemokine immunoadjuvant", Human Vaccines & Immunotherapeutics,vol. 8, No. 11, 2012, p. 1607-p. 1619.
Kazutoshi Sayama et al., "CCL25 in mouse breast milk promotes growth of newborn mouse and development of immune function", The Japanese Society of Nutrition and Food Science 70th Annual Meeting Collection of general seminar topics, Apr. 25, 2016, p. 37-p. 40.
Kunio Hieshima, "CCL25 and CCL28 are involved in homing of IgA antibody producing cells to intestinal tract", Clinical Immunology,vol. 43, No. 5, 2005, p. 584-p. 588.
Meurens,F. et al., "Expression of mucosal chemokines TECK/CCL25 and MEC/CCL28 during fetal development of the ovine mucosal immune system", Immunology, vol. 120, 2007, p. 544-p. 555.
Masaki Takenaka et al., "Expression of CCL25 in mammary gland tissues of pregnant and lactating mice", Proceedings of the Annual Meeting of Japan Society for Bioscience, Biotechnology, and Agrochemistry, 2010, p. 227.
Masaki Takenaka, Kazutoshi Sayama, "Expression of CCL25 chemokine in mammary gland of pregnant and lactating mice", Science Exchange Forum in 2009 11th Shizuoka Life Science Symposium, Mar. 5, 2010, p. 19.
International Search Report dated Sep. 20, 2016 issued in International Application No. PCT/JP2016/068098.
International Preliminary Report on Patentability Form PCT/IB/338 dated Dec. 21, 2017 in International Application No. PCT/JP2016/068098 with English translation.
Andreas, Nicholas J. et al.: "Human breast milk: A review on its composition and bioactivity", *Early Human Development* 91 (2015) pp. 629-635.
Ballard, O. et al,: Human Milk Composition: Nutrients and Bioactive Factors, *Pediatr Clin North Am.*, Feb. 2003; 60(1): pp. 49-74.

* cited by examiner

*Primary Examiner* — Joanne Hama
*Assistant Examiner* — Jegatheesan Seharaseyon
(74) *Attorney, Agent, or Firm* — Ostrolenk Faber LLP

(57) ABSTRACT

The present invention discloses immune function development promoters and growth promoters comprising CCL25. The development of immune functions in a subject can be promoted by ingesting an immune function development promoter according to the present invention. Moreover, growth of a subject can be promoted by ingesting a growth promoter according to the present invention.

6 Claims, 4 Drawing Sheets
Specification includes a Sequence Listing.

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: GAPDH Forward Primer

<400> SEQUENCE: 1
```

```
gggtgtgaac catgagaagt                                              20

<210> SEQ ID NO 2
<211> LENGTH: 19
<212> TYPE: DNA
<213> ORGANISM: Artificial Sequence
<220> FEATURE:
<223> OTHER INFORMATION: GAPDH Reverse Primer

<400> SEQUENCE: 2
gactgtggtc atgagtcct                                               19

<210> SEQ ID NO 3
<211> LENGTH: 20
<212> TYPE: DNA
<213> ORGANISM: Artificial Sequence
<220> FEATURE:
<223> OTHER INFORMATION: CCL25 Forward Primer

<400> SEQUENCE: 3
ccatcagcag cagtaagagg                                              20

<210> SEQ ID NO 4
<211> LENGTH: 20
<212> TYPE: DNA
<213> ORGANISM: Artificial Sequence
<220> FEATURE:
<223> OTHER INFORMATION: CCL25 Reverse Primer

<400> SEQUENCE: 4
ctgtagggcg acggttttat                                              20

<210> SEQ ID NO 5
<211> LENGTH: 19
<212> TYPE: DNA
<213> ORGANISM: Artificial Sequence
<220> FEATURE:
<223> OTHER INFORMATION: CCR9 Forward Primer

<400> SEQUENCE: 5
gcctgagcag ggagattat                                               19

<210> SEQ ID NO 6
<211> LENGTH: 14
<212> TYPE: DNA
<213> ORGANISM: Artificial Sequence
<220> FEATURE:
<223> OTHER INFORMATION: CCR9 Reverse Primer

<400> SEQUENCE: 6
gagcagacag agtg                                                    14
```

IMMUNE FUNCTION DEVELOPMENT PROMOTER AND GROWTH PROMOTER

CROSS-REFERENCE TO RELATED APPLICATIONS

The present application is a 35 U.S.C. §§ 371 national phase conversion of PCT/JP2016/068098, filed Jun. 17, 2016, which claims priority to Japanese Patent Application No. 2015-123682, filed Jun. 19, 2015, the contents of both of which are incorporated herein by reference. The PCT International Application was published in the Japanese language.

TECHNICAL FIELD

The present invention relates to an immune function development promoter and a growth promoter.

BACKGROUND ART

The ingestion of breast milk plays an important role in the acquisition of early immune functions by newborns. In particular, colostrum secreted just after delivery contains IgA antibodies and many substances involved in immune functions and plays an important role in the defense of newborns against infection. The substances involved in the immune function include proteins called chemokines and CXCL8 (IL-8), CCL5 (RANTES), and CCL28 are known as chemokines comprised in the breast milk. However, for example, it has been reported that almost no expression of CCL28 is found in the mammary tissue at the time of colostral production and secretion. Thus, it is still unknown how chemokines are involved in the acquisition of immunity by the newborns through the colostral ingestion.

Other than the above chemokines, chemokines discovered in the murine and human thymus and involved in intestinal immunity include Chemokine (C-C motif) ligand 25 (CCL25). The possibility that CCL25 is involved in the transition of IgA to the colostrum in the mammary tissue as a function of CCL25 in the mother's body has so far been reported (Non Patent Literature 1). However, it has not been clear yet how CCL25 serves in the acquisition of immunity by newborns through the colostral ingestion.

CITATION LIST

Non Patent Literature

Non Patent Literature 1: Masaki Takenaka and Kazutoshi Sayama, "Expression of CCL25 chemokine in murine mammary gland during pregnancy and lactation (in Japanese)", Mar. 5, 2010, Proceedings of the 11th Shizuoka Life Science Symposium, p. 19

SUMMARY OF INVENTION

Technical Problem

An object of the present invention is to identify a new function of CCL25.

Solution to Problem

The present inventors have surprisingly found that CCL25, which has been considered to be involved in the transition of IgA to milk by the expression in the mother's body, is comprised in the milk itself and has the functions to promote the development of immune functions and to promote growth by directly acting on the subject that ingests the milk, thereby completing the present invention. Accordingly, the present invention provides the following [1] to [6].

[1] An immune function development promoter comprising CCL25.

[2] The immune function development promoter according to [1] for an infant.

[3] The immune function development promoter according to [1] or [2] for oral ingestion.

[4] A growth promoter comprising CCL25.

[5] The growth promoter according to [4] for an infant.

[6] The growth promoter according to [4] or [5] for oral ingestion. Furthermore, the present invention provides the following [7] to [24].

[7] Use of CCL25 for production of an immune function development promoter.

[8] The use according to [7], wherein the immune function development promoter is for an infant.

[9] The use according to [7] or [8], wherein the immune function development promoter is for oral ingestion.

[10] Use of CCL25 for production of a growth promoter.

[11] The use according to [10], wherein the growth promoter is for an infant.

[12] The use according to [10] or [11], wherein the growth promoter is for oral ingestion.

[13] CCL25 for use in promotion of immune function development in a subject.

[14] The CCL25 according to [13], wherein the subject is an infant.

[15] The CCL25 according to [13] or [14], wherein the subject orally ingests the CCL25.

[16] CCL25 for use in promotion of growth of a subject.

[17] The CCL25 according to [16], wherein the subject is an infant.

[18] The CCL25 according to [16] or [17], wherein the subject orally ingests the CCL25.

[19] A method for promoting immune function development in a subject, comprising administering CCL25 to a subject in need thereof.

[20] The method according to [19], wherein the subject is an infant.

[21] The method according to [19] or [20], wherein the CCL25 is orally administered.

[22] A method for promoting growth of a subject, comprising administering CCL25 to a subject in need thereof.

[23] The method according to [22], wherein the subject is an infant.

[24] The method according to [22] or [23], wherein the CCL25 is orally administered.

Advantageous Effects of Invention

The development of immune functions in a subject can be promoted by ingesting an immune function development promoter according to the present invention. Moreover, growth of a subject can be promoted by ingesting a growth promoter according to the present invention.

DESCRIPTION OF EMBODIMENTS

Figure 1:
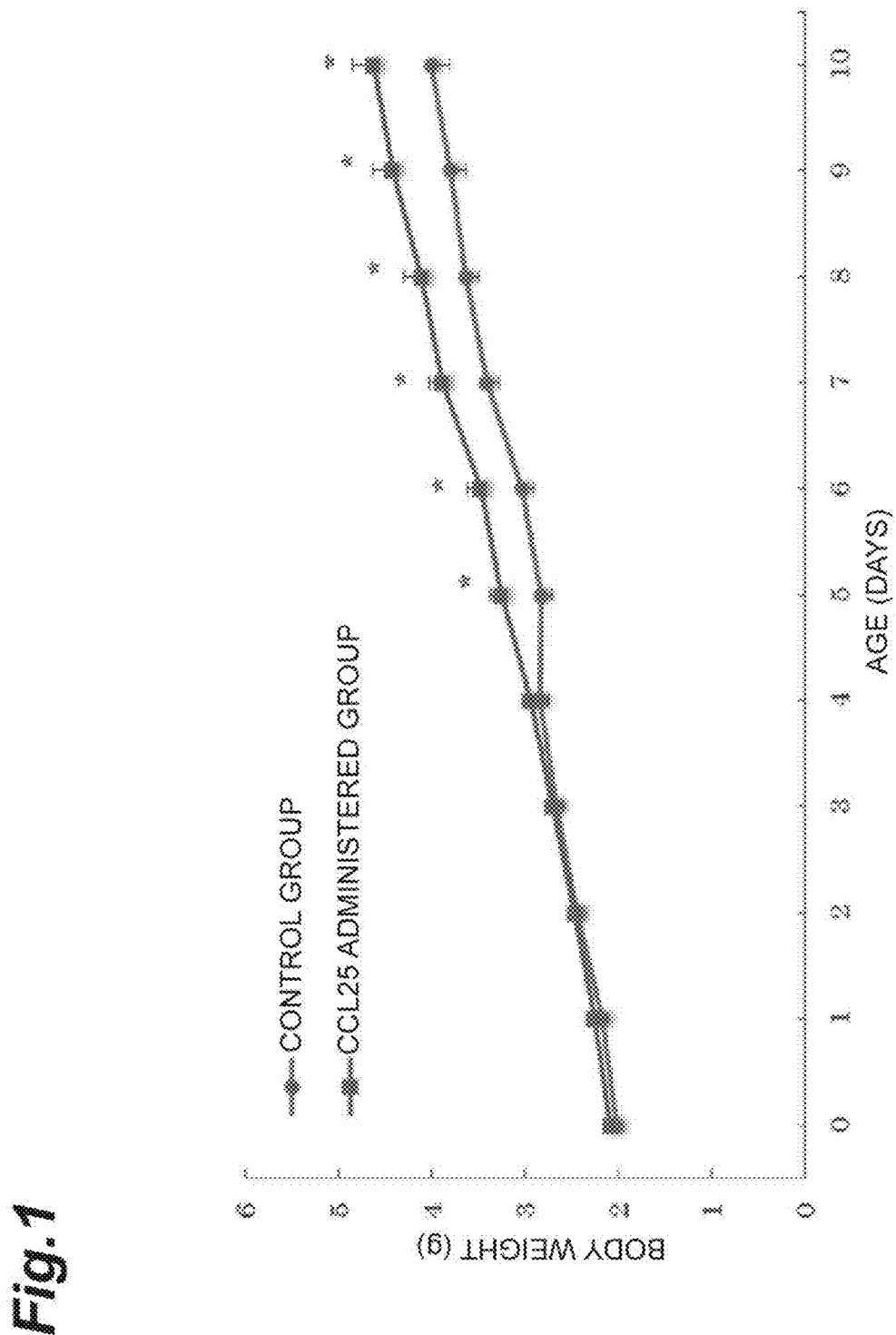
FIG. 1 is a graph comparing over time the weight gain of the group of neonate mice artificially reared with artificial milk comprising CCL25 (CCL25 administered group) and the group of neonate mice artificially reared with artificial milk comprising no CCL25 (control group). * indicates significant difference from the control group (P>0.05).

Immune function development promoters and growth promoters according to the present embodiments are for mammals including humans and nonhuman animals and preferably for humans.

In the present embodiments, the immune function development promoters and growth promoters are preferably for infants and more preferably for newborns. An infant means a child reared with breast milk or artificial milk. Without bound to the length of time after birth, in humans, for example, an infant may mean a child within 1 year after birth and a newborn may mean a child within 28 days after birth. Infants and newborns in the nonhuman animals mean individuals at ages corresponding to human infants and newborns, respectively.

The immune function development promoters and growth promoters comprising CCL25 according to the present embodiments are not particularly limited as long as they are compositions comprising CCL25 in an active state, but do not include milk itself obtained from the mother's body.

The CCL25 to be used may be prepared by a known method or a commercially available product.

The mode of administration of the immune function development promoters and growth promoters according to the present embodiments is not particularly limited and the promoters may be for oral ingestion, enteral administration, transvenous administration, or the like, but preferably for oral ingestion.

The form of the immune function development promoters and growth promoters according to the present embodiments for oral ingestion by a subject is not particularly limited, and the promoters may be used in a medium suitable for oral ingestion by the subject, but preferably used in artificial milk.

The artificial milk means milk that is artificially produced or processed, but not milk as it is obtained from the mother's body. Examples thereof include formula milk and liquid modified milk for infants, for premature infants, and for medicine.

The immune function development promoter means a composition that is recognized to promote the development of immune functions of a subject when the composition is ingested by or administered to the subject in comparison with a subject which the composition is not ingested by or administered to. Examples of an indicator that may be used to determine whether an immune function is promoted include the expression level of a gene and/or a protein that is involved in the immune system; the weight of an organ that is an immune organ, such as the intestines (the large and small intestines), the spleen, or the thymus, relative to the body weight; the number of cells involved in the immune system, such as IgA-producing cells, lymphocytes (T cells such as killer and helper T cells, B cells, and natural killer cells), double-negative cells, or double-positive cells; and the number and size of Peyer's patches in the small intestine. More specifically, if the expression level of a gene and/or a protein whose expression level is increased when the immune function is working or the weight of the intestine, the spleen, or the thymus relative to the body weight is significantly higher, if the number of IgA-producing cells, the number of lymphocytes, or the number of Peyer's patches is significantly more, and if the sizes of Peyer's patches are significantly larger in comparison with a subject which the composition is not ingested by or administered to, then the development of the immune function can be determined to be promoted by the ingestion or administration of the composition.

Examples of the gene and/or protein whose expression level is increased when the immune function is working include surface markers of various immune cells, various cytokines, and immunoglobulins including IgA. Examples of the immune organ include, besides the intestines, the spleen, and the thymus, the lymph node and the bone marrow and examples of the cells involved in the immune system include, besides the IgA-producing cells, lymphocytes (T cells such as killer and helper T cells, B cells, and natural killer cells), double-negative cells, double-positive cells, macrophages, and leukocytes.

The growth promoter means a composition that is recognized to promote the growth of a subject when the composition is ingested by or administered to the subject in comparison with a subject which the composition is not ingested by or administered to. Examples of an indicator that may be used to determine whether the growth is promoted include the expression level of a gene and/or a protein involved in growth and the body weight, the muscle mass, or the organ weight of the subject. More specifically, if the expression level of the gene and/or protein whose expression level is increased when the growth is promoted or the body weight, the muscle mass, or the organ weight of the subject is significantly higher in comparison with a subject which the composition is not ingested by or administered to, then the growth can be determined to be promoted by the ingestion or administration of the composition.

Examples of the gene and/or protein whose expression level is increased when the growth is promoted include a growth hormone, a thyroid hormone, and glucocorticoid.

EXAMPLES

The present invention will be described in more detail with reference to the following Examples, but the present invention is not limited by these Examples.

(Neonate Mice Experimental Group)

The day when the copulation was confirmed was set at day 0 of pregnancy and the female was isolated alone on the day before giving birth (day 19 of pregnancy). The day of giving birth was set at day 0 and 6 groups: day 0 after birth (the parent was subjected to a cesarean operation), day 1 after birth, day 2 after birth, day 5 after birth, and day 10 after birth, and day 21 after birth (after weaning) were made. The intestines (the small and large intestines) were extracted from neonates at each stages.

(Preparation of Intestine Sample)

Murine neonates were euthanized by excess inhalation of diethyl ether according to the standard on the use of poison and the intestines (the small and large intestines) were extracted. The large intestine was soaked in RNAlater (Takara Bio Inc.) and impregnated with the reagent at 4° C. overnight and then stored at −80° C. The small intestine was divided into 3 equal portions and they were respectively (1) soaked in RNAlater (Takara Bio Inc.) and impregnated with the reagent at 4° C. overnight and then stored at −80° C. as a sample to be used in real-time PCR; (2) put in a plastic cryomold (square type 1, Sakura Finetek Japan Co., Ltd.) with the mounting medium Tissue-Tek O. C. T. compound (Sakura Finetek Japan Co., Ltd.) and rapidly frozen on dry ice to prepare a block for cryosection and stored at −80° C. as a sample for use in immunostaining; and (3) soaked in 4% paraformaldehyde fixation liquid for 24 to 36 hours for fixation as a sample for use in Hematoxylin and Eosin tissue staining (Hematoxylin and Eosin Stain, HE Stain). The sample for tissue staining was washed 3 to 4 times with 1×PBS after the fixation and stored in a 70% ethanol solution for the preparation of tissue preparations.

(Real-Time PCR)

Total RNA was prepared using RNeasy Mini Kit (QIAGEN N.V.) according to a protocol. Super Script™ First-Strand Synthesis System (Invitrogen) was used to synthesize cDNA. 10 μl of Fast Start Essential DNA Green Master 2×conc. (Roche), 1 μl of Sense primer (10 μM), 1 μl of Anti-sense primer (10 μM), 1 μl of cDNA, and 7 μl of Fast Start Essential DNA Green Master $H_2O$ (Roche) were added to a tube for real-time PCR to make a total volume of reaction of 20 μl. Then, real-time PCR was conducted using Light Cycler™ Nano (Roche). The primers (Sigma-Aldrich) used for the real-time PCR were GAPDH (size of PCR product 136 bp): 5'-GGGTGTGAACCATGAGAAGT-3' (SEQ ID NO: 1, forward) and 5'-GACTGTGGTCAT-GAGTCCT-3' (SEQ ID NO: 2, reverse), CCL25 (size of PCR product 131 bp): 5'-CCATCAGCAGCAGTAAGAGG-3' (SEQ ID NO: 3, forward) and 5'-CTGTAGGGCGACG-GTTTTAT-3' (SEQ ID NO: 4, reverse), and CCR9 (size of PCR product 110 bp): 5'-GCCTGAGCAGGGAGATTAT-3' (SEQ ID NO: 5, forward) and 5'-GAGCAGACAGAGTG-3' (SEQ ID NO: 6, reverse). The genes analyzed were CCL25, CCR9 and GAPDH (as an internal standard). The reaction conditions for the genes were as follows: under conditions of initial denaturation at 95° C. for 3 minutes and then CCL25: total 40 cycles of thermal denaturation (95° C., 60 seconds), annealing (55° C., 50 seconds), and the elongation reaction (72° C., 60 seconds); CCR9: total 45 cycles of thermal denaturation (95° C., 60 seconds), annealing (58° C., 50 seconds), and the elongation reaction (72° C., 60 seconds); GAPDH: total 45 cycles of thermal denaturation (95° C., 60 seconds), annealing (55° C., 50 seconds), and the elongation reaction (72° C., 60 seconds), the amplification was conducted.

(Immunohistochemical Staining)

The intestine tissue stored at −80° C. was equilibrated at −20° C. for approximately 20 minutes (to prevent crush at the time of preparation of sections) before the preparation of sections. Subsequently, the intestine tissue block was sliced into thin sections with a thickness of 8 μm with a cryostat and a section was attached on a silane-coated no-fluorescence microscope slide (FRC-11, Matsunami Glass Ind., Ltd.). The section was dried on the slide and then immersed in cold acetone at −20° C. for 10 minutes and dried with air. The section was washed with a washing buffer (1×PBS) for 5 minutes three times and then immunostained. For immunostaining of each of CCL25 and IgA, a primary antibody and a secondary antibody were used. Each section was blocked with a PBS blocking solution comprising 1% BSA at room temperature for 1 hour. The blocking solution was removed and a primary antibody diluted with the blocking solution was added to each section. The sections were incubated at 4° C. overnight. The primary antibody solutions were removed and the sections were washed with 1×PBS for 5 minutes three times. To each section, a secondary antibody diluted with a PBS blocking solution comprising 1% BSA was added. The sections were incubated at room temperature for 2 hours and then the secondary antibodies were removed. The sections were washed with 1×PBS for 5 minutes three times. Subsequently, the sections were enclosed on microscope slides with a water-soluble mounting medium (Thermo Scientific) and observed under a fluorescence stereomicroscope (MZ10F, Leica Microsystems). The antibodies used for the immunohistochemical staining were CCL25: Goat anti-mouse CCL25/TECK antibody (primary antibody, R&D Systems, Inc.), Fluorescein (FITC)-conjugated AffiniPure Rabbit Anti-Goat++ IgG (H+L) (secondary antibody, Jackson Immuno Research Inc.), IgA: Goat anti-mouse IgA affinity Purified (primary antibody, Bethyl Laboratories Inc.), Rhodamine (TRITC)-conjugated AffiniPure Donkey Anti-Goat++ IgG (H+L) (secondary antibody, Jackson Immuno Research Inc.), which were all used at 1:100 dilution.

(Statistical Analysis)

All statistical processing of experimental results was conducted using t-test and, unless specifically indicated, the statistical significance level was set at 5% ($P>0.05$).

(Preparation of Artificial Milk)

An artificial milk for mouse was prepared in reference to the literature (Biosci. Biotechnol. Biochem., 2007, 71 (10), 2420-2427 and Experimental animals, 2006, 55 (4), 391-397) on the artificial rearing using artificial milk for mouse, with modification of the fat content from 16% to 18%. The method for preparing the artificial milk is described below. Firstly, Casein mixture was prepared.

(a) The 3 amino acids, serine (0.2875 g), cysteine (0.225 g) and tryptophan (0.27 g) were added to 200 ml of an alkaline aqueous solution comprising NaOH (0.25 g) and KOH (1.5 g) (which was constantly stirred with a stirrer, 60 to 70° C.).

(b) Casein (40.0 g) was added to and dissolved in the alkaline aqueous solution. This Casein mixture was sterilized in a boiling water bath for 30 minutes. Next, micelles of caseinate were prepared.

(c) Calcium and magnesium were added to Casein mixture. $CaCl_2.2H_2O$ (1.7 g), $GlyCaPO_4$ (8 g), and $MgCl_2.6H_2O$ (1.9 g) were dissolved in 50 ml of distilled water (which was autoclaved at 121° C. for 10 minutes) and the mixture was homogenized with a Polytron-like mixer. This was added to Casein mixture slowly (with continuation of mixing in the homogenizer).

(d) $CaCO_3.2H_2O$ (2.5 g) and Ca-citrate (1.2 g) were dissolved in 25 ml of distilled water and, after autoclaving, the solution was added to Casein mixture slowly.

(e) $Na_2HPO_4$ (0.8 g) and $KH_2PO_4$ (0.08 g) were dissolved in 12.5 ml of distilled water and, after sterilization with an autoclave, the solution was added to Casein mixture.

(f) After sterilization with an autoclave, a lactose aqueous solution (obtained by dissolving 18.91 g of lactose in 55 ml of distilled water) was added to Casein mixture slowly.

(g) $FeSO_4.7H_2O$ (0.48 g) and Citrate-$H_2O$ (0.01 g) were dissolved in 5 ml of distilled water. 2.5 ml of the resulting solution, $ZnSO_4.7H_2O$ (0.3 g), $CuSO_4.5H_2O$ (0.075 g), and $MnSO_4.5H_2O$ (0.0125 g) were dissolved in 6.25 ml of distilled water. 1.25 ml of the resulting solution, NaF (0.00775 g) and KI (0.0125 g) were dissolved in 6.25 ml of distilled water. 1.25 ml of the resulting solution was added to Casein mixture. This procedure was conducted with constant stirring after sterilization with Millipore Filtration (0.45 μm).

(h) Subsequently, Whey Protein Isolate (40 g) and Whey Protein Hydrolysate (50 g) were dissolved in 250 ml of sterilized distilled water. This solution was added to Casein mixture that was cooled to 40° C. or lower with stirring.

(i) Carnitine (0.08 g), picolinic acid (0.04 g), ethanolamine (0.068 g), and taurine (0.3 g) were dissolved in 5 ml of distilled water. 2.5 ml of the resulting solution was added to Casein mixture.

(j) In a neutralized solution (neutralized to pH 7.0 with 5N NaOH) of choline dihydrogen citrate (1.47 g) dissolved in 18.375 ml of distilled water, a water-soluble vitamin mixture (cyanocobalamin (0.0119 mg), biotin (0.18 mg), folic acid (0.78 mg), thiamine hydrochloride (8.81 mg), pyridoxine hydrochloride (1.25 mg), riboflavin sodium phosphate (12.15 mg), calcium pantothenate (26.43 mg), p-aminobenzoic acid (44.04 mg), nicotinic acid (49.88 mg), sodium ascorbate (674 mg), and 4-inositol (487.25 mg)) was dissolved. 17.5 ml of the resulting solution was added to Casein mixture.

(k) Fat-solubility vitamins (a mixture comprising vitamin $K_3$ (19.825 mg), vitamin E: α-tocopherol (23.45 mg), and vitamins A and D) and 6 edible oils (palm oil (53.85 g), coconut oil (44.9 g), corn oil (17.955 g), medium-chain triglyceride oil (26.9325 g), soybean oil (35.91 g), and cholesterol (0.4 g)) were sterilized in a boiling water bath for 30 minutes. This oily solution was cooled to 40 to 50° C. and then added to Casein mixture with stirring.

(l) This last mixture was homogenized three times under high pressure conditions (180 kg/cm$^2$).

(m) After the homogenization, the artificial milk was sterilely dispensed into 50 ml sterilized polypropylene bottles and frozen at −20° C.

(n) The frozen artificial milk was sterilized by gamma irradiation (30 kGy) and stored at −20° C. until lactation experiments.

(Mice Used in Artificial Lactation Experiment)

10 to 12 week-old ddY mice (Japan SLC Inc.) and neonates of ddY mice were used.

(Artificial Lactation Experiment)

As a preliminary experiment, artificial lactation with the artificial milk was started within 3 hours after the cesarean operation. Artificial lactation for 32 neonates delivered by the cesarean operation resulted in the death of approximately 43% (14) neonate mice on day 3. By day 9, all neonate mice died. Based on the result, it was decided to feed neonates that have been breast-fed till an age of 2 days after birth, artificial milk once in 3 hours from an age of 3 days after birth in these Examples.

(Hematoxylin Staining)

The small intestine from the mice reared by artificial lactation was extracted and the small intestine (from the duodenum to jejunum) was pinned and immersed and fixed in 10% formalin solution for 3 hours or more. After the fixation, the intestine was washed with distilled water several times and stained with Mayer's Hematoxylin Solution for 7 minutes. Subsequently, the intestine was washed with distilled water once and then with flowing water for 1 hour.

Example 1: Observation of Change Over Time of Expression of CCL25 and CCR9 and IgA-Producing Cells in Neonate Intestine The expression of CCL25 mRNA in the intestine tissue was analyzed by real-time PCR. The result indicated that the CCL25 mRNA expression level in the small intestine relative to the expression level in the group of day 21 after birth, the weaning time, which was defined to be 1, was 0.12±0.07 in the group of day 0 after birth, 0.09±0.06 in the group of day 1 after birth, 0.39±0.04 in the group of day 2 after birth, 0.62±0.003 in the group of day 5 after birth, and 0.70±0.05 in the group of day 10 after birth. In summary, the expression level of CCL25 mRNA began to increase from day 2 after birth and the level increased over time and the expression level was significantly increased in the groups of day 5 to day 21 after birth in comparison with the group of day 0. The expression level in the large intestine was 0.41±0.04 in the group of day 0 after birth, 0.33±0.01 in the group of day 1 after birth, 0.27±0.02 in the group of day 2 after birth, 0.08±0.006 in the group of day 5 after birth, 0.09±0.006 in the group of day 10 after birth, and the highest in the group of day 21 after birth.

For CCR9, the only receptor of CCL25, the expression of mRNA in the intestine tissue was analyzed by real-time PCR. The result indicated that the expression in the small intestine relative to that in the group of day 21 after birth, which was defined to be 1, was 0.15±0.04 in the group of day 0 after birth, 0.25±0.006 in the group of day 1 after birth, 0.02±0.01 in the group of day 2 after birth, 0.50±0.01 in the group of day 5 after birth, and 0.7±0.01 in the group of day 10 after birth. In summary, the expression level of CCR9 mRNA in comparison with day 0 after birth began to significantly increase from day 5 after birth and the level increased over time. The level of CCR9 mRNA in the group of day 21 after birth exhibited the highest value. The expression level in the large intestine was 0.006±0.0005 in the group of day 0 after birth, 0.036±0.008 in the group of day 1 after birth, 0.005±0.001 in the group of day 2 after birth, 0.005±0.0003 in the group of day 5 after birth, and 0.004±0.0004 in the group of day 10 after birth. The expression level of CCR9 mRNA in the group of day 1, day 2, day 5, and day 10 after birth exhibited low values and the value in the group of day 21 after birth was revealed to be the peak.

Next, the mRNA expression levels of CCL25 and CCR9 in the large intestine and the small intestine in the group of day 10 after birth were compared. The result indicated that the CCL25 mRNA expression level in the large intestine relative to the expression level in the small intestine, which was defined to be 1, was 0.07±0.009. The CCR9 mRNA expression level in the large intestine relative to the expression level in the small intestine, which was defined to be 1, was 0.06±0.003. The expression level of CCL25 mRNA and CCR9 mRNA in the large intestine exhibited significantly lower values in comparison with those in the small intestine. From this result, CCL25 in the neonate intestine was confirmed to be mainly expressed in the small intestine, similarly to that after the weaning, when the intestine functions are established.

Next, the change over time of CCL25 in the small intestine tissue was examined by the immunohistochemical staining with the CCL25 antibody. An immunohistochemical staining was conducted for the expression of CCL25 in the small intestine tissue using the CCL25-FITC antibody. The observation of the positive sites for the fluorescent staining with a fluorescence stereomicroscope confirmed almost no expression of CCL25 in the chorioepithelium of the small intestine in the groups of day 0, day 2, and day 5 after birth, but confirmed the expression of CCL25 in the chorioepithelium in the groups of day 1, day 10, and day 21 after birth.

Next, the change over time of IgA-producing cells in the small intestine tissue was examined using the IgA antibody by the immunohistochemical staining. An immunohistochemistry staining was conducted for the expression of IgA-producing cells in the small intestine tissue using the IgA-RITC antibody. The observation with a fluorescence stereomicroscope after the fluorescent staining confirmed almost no expression of IgA-producing cells in the chorioepithelium of the small intestine in the groups of day 0, day 2, and day 5 after birth, but confirmed the presence of IgA-producing cells in most of the chorioepithelium in the group of day 10 after birth and all of the chorioepithelium in the group of day 21 after birth.

Example 2: Effect of CCL25 on Weight Gain

Following the method described in the documents by Yajima et al. (Biosci. Biotechnol. Biochem., 2007, 71 (10), 2420-2427 and Experimental animals, 2006, 55 (4), 391-397), neonate mice were breast-fed till an age of 2 days after birth and then reared by artificial lactation with various artificial milk starting from an age of 3 days. Neonate mice were divided into 2 groups; (1) a group (CCL25 administered group) for which 0.5 µg/ml of CCL25 (Recombinant Mouse CCL25 (TECK), Bio-Legend Inc.) was added to artificial milk and (2) a group (control group) for which no CCL25 antigen was added to artificial milk.

The examination of the change of body weight of the neonate mice reared by artificial lactation indicated that the body weights of the neonate mice in the CCL25 administered group were substantially equal to the body weights of mice in the control group till an age of 4 days after birth, but significantly increased in comparison with those of the control group after an age of 5 days (FIG. 1).

Example 3 Effect of CCL25 on Weight of Immune Organ and Peyer's Patch

Figure 2:
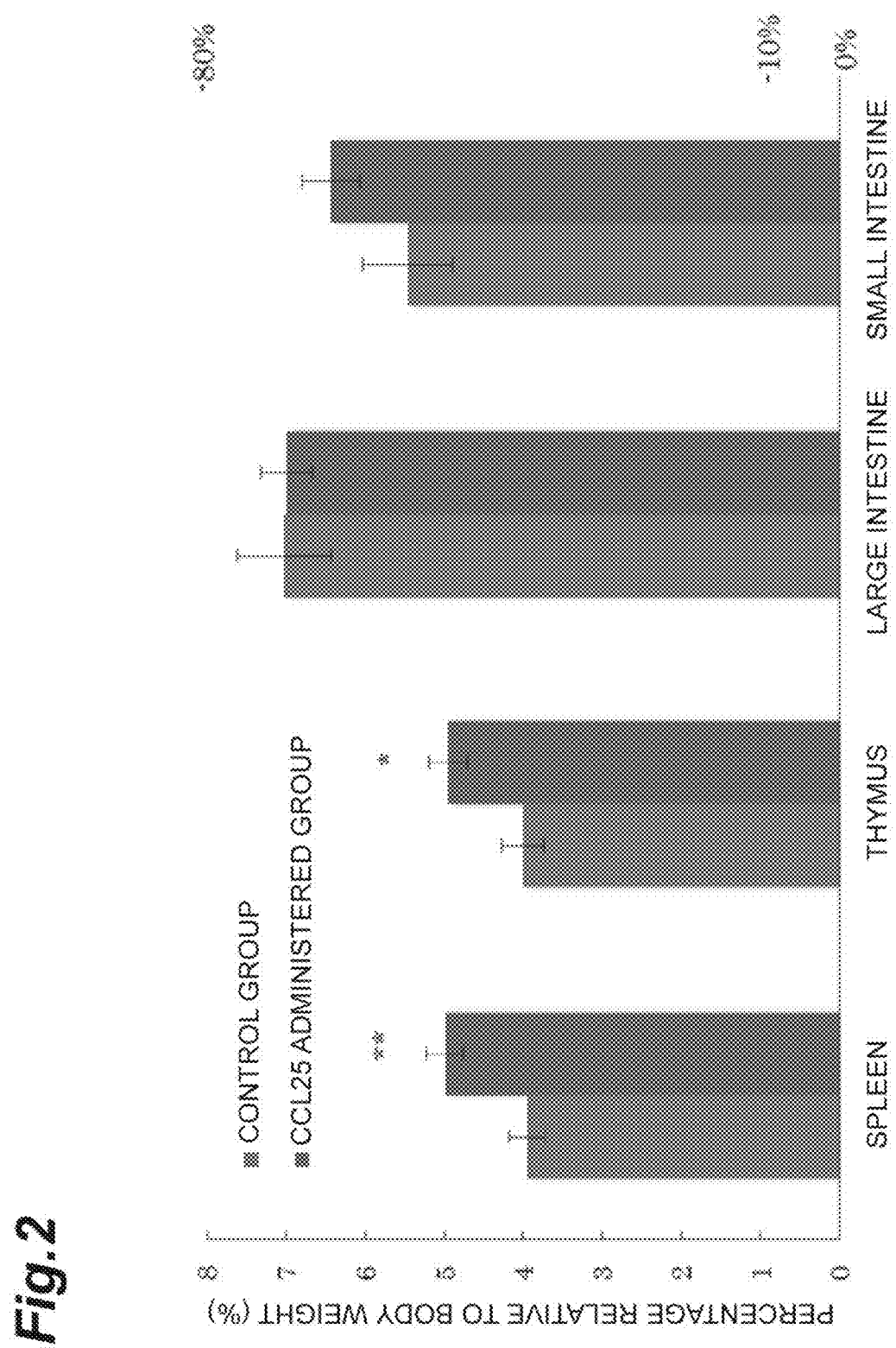
FIG. 2 is a graph comparing the organ weights relative to the body weight in the CCL25 administered group and the control group. * and ** indicate significant difference from the control group (*: P>0.05, **: P>0.01).

Neonate mice were divided into a CCL25 administered group and a control group similarly to Example 2, artificially reared for 7 days till an age of 10 days, and then autopsied. The intestines (the small and large intestines), the spleen, and the thymus were extracted and the weights of the organs were compared between the CCL25 administered group and the control group. The comparison of the weights of the spleen, which is an immune organ, the thymus, and the intestines relative to the body weight indicated that while the spleen (SP) was 3.95%±0.05, the thymus (Thy) was 4.00%±0.06, the large intestine (LI) was 7.02%±0.08, and the small intestine (SI) was 5.46%±0.10 in the control group, the weight of the spleen (SP) was 4.99%±0.058, the weight of the thymus (Thy) was 4.95%±0.059, the weight of the large intestine (LI) was 6.99%±0.04, and the weight of the small intestine (SI) was 6.44%±0.06 in the CCL25 administered group. The tendency that the weight of the small intestine was higher in the CCL25 administered group than that in the control group was found and the weights of the spleen and the thymus were significantly higher (FIG. 2). In contrast, the weight of the large intestine relative to the body weight in the control group and the CCL25 administered group exhibited almost the same value.

Moreover, the small intestine stained with hematoxylin was observed with a microscope and the number of Peyer's patches in the small intestine was counted to calculate the number of Peyer's patches per animal. Furthermore, the major axis and the minor axis of each Peyer's patch were measured and the size of Peyer's patches per animal was calculated with assuming the average of the major and minor axes to be the size of the Peyer's patch. The comparison of the numbers and the sizes of Peyer's patches in the control group and the CCL25 administered group indicated no difference in the sizes of individual Peyer's patches, but the tendency that the number of the Peyer's patches is higher in the CCL25 administered group than in the control group.

Example 4 Effect of CCL25 on Expression of CCL25 mRNA and CCR9 mRNA in Intestine Tissue Examination of the expression of CCL25 mRNA in the intestine tissue indicated that the expression level of CCL25 mRNA in the small intestine in the CCL25 administered group relative to that in the control group, which was defined to be 1, was 0.79±0.11. There was no significant difference, but the tendency that the expression level was higher in the control group was found. Moreover, examination of the expression level of CCR9 mRNA in the intestine tissue indicated that the expression level of CCR9 mRNA in the small intestine in the CCL25 administered group relative to that in the control group, which was defined to be 1, was 1.29±0.16. There was no significant difference, but the tendency that the expression level was higher in the CCL25 administered group was found.

Figure 3:
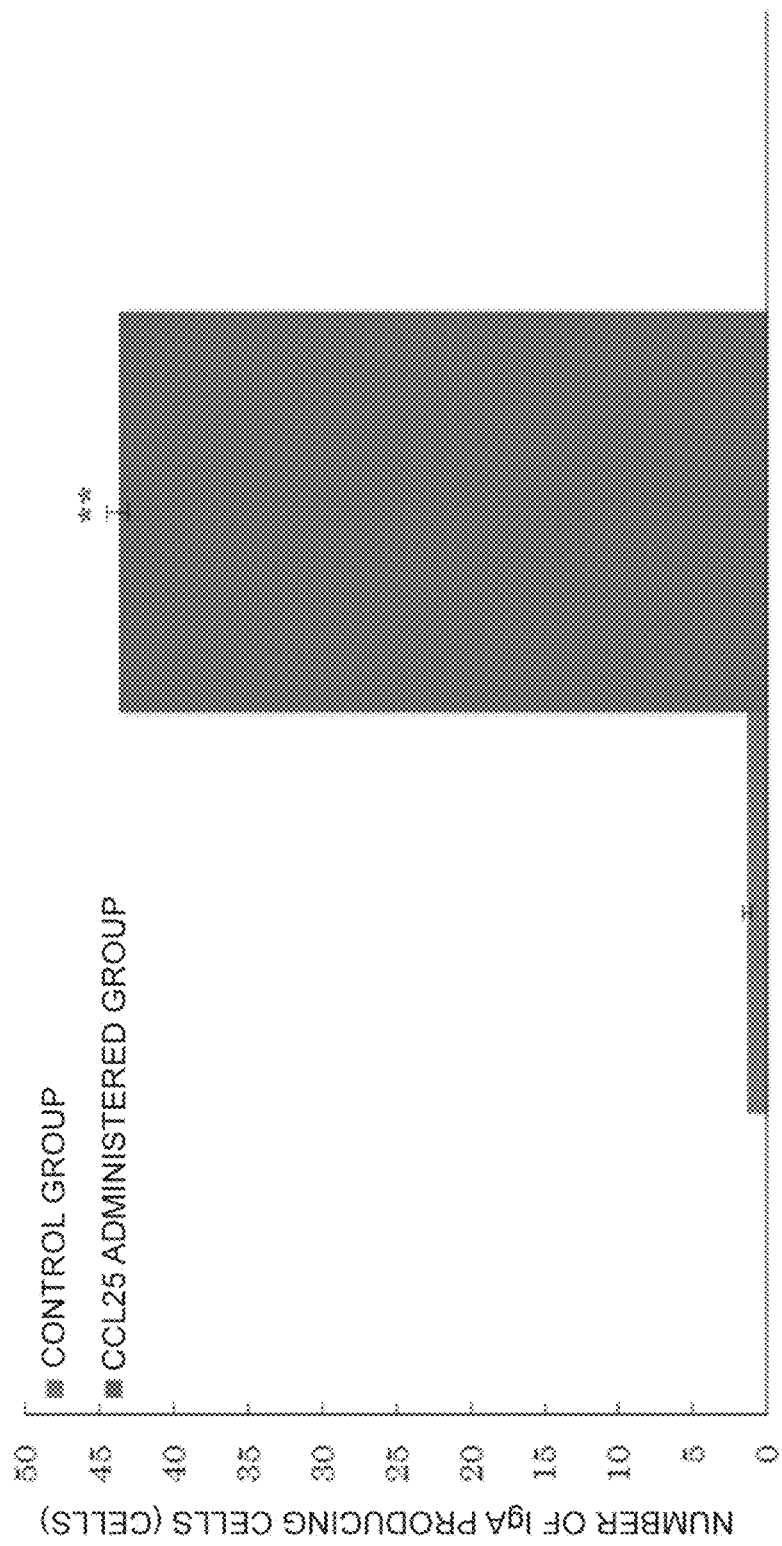
FIG. 3 is a graph comparing the number of IgA-producing cells in the intestine in the CCL25 administered group and the control group. * indicates significant difference from the control group (P>0.01).

Example 5 Effect of CCL25 on the Number of IgA-Producing Cells in Intestinal Villi in the Small Intestine The immunohistochemistry staining of IgA-producing cells in the small intestine tissue was conducted using the IgA-RITC antibody. 7 villi in one intestine (the small intestine) were selected and the number of positive IgA-producing cells in the villi was counted to compare the control group and the CCL25 administered group. While almost no IgA-producing cells were confirmed in the 7 villi and the number of the cells was 1.33±0.2 in the control group, the number was 43.75±1.24 and significantly higher in the CCL25 administered group (FIG. 3). From this result, it was revealed that CCL25 in milk is necessary to induce IgA till day 10 after delivery.

Example 6 Effect of CCL25 on the Number of Cells in Thymus

Experimental animals used were 10 to 20 week-old ddY mice (Japan SLC Inc.) and neonates of ddY mice.

Following the method described in the documents by Yajima et al. (Biosci. Biotechnol. Biochem., 2007, 71 (10), 2420-2427 and Experimental animals, 2006, 55 (4), 391-397), neonate mice were breast-fed till an age of 2 days after birth and then reared by artificial lactation with various artificial milk for 8 days from an age of 2 days to an age of 10 days. Neonate mice were divided into 2 experimental groups: (1) a group (CCL25 administered group) for which 0.5 µg/mL of CCL25 (Recombinant Mouse CCL25 (TECK), Bio-Legend Inc.) was added to artificial milk and (2) a group (control group) for which no CCL25 antigen was added.

An artificial milk for mouse was prepared in reference to the literature (Biosci. Biotechnol. Biochem., 2007, 71 (10), 2420-2427 and Experimental animals, 2006, 55 (4), 391-397) on the artificial rearing using artificial milk for mouse, with modification of the fat content from 16% to 18%. The method for preparing the artificial milk is described below.

(a) NaOH (1 g) and KOH (6 g) were dissolved in 800 ml of distilled water (an alkaline aqueous solution). The 3 amino acids, serine (1.15 g), cysteine (0.9 g), and tryptophan (1.08 g) were added to the alkaline aqueous solution (which was constantly stirred with a stirrer, 60 to 70° C.).

(b) Casein (160.0 g) was added to and dissolved in the alkaline aqueous solution. This Casein mixture was sterilized in a boiling water bath for 30 minutes.

(c) $CaCl_2 \cdot 2H_2O$ (6.8 g), $GlyCaPO_4$ (32 g), and $MgCl_2 \cdot 6H_2O$ (7.6 g) were dissolved in 200 ml of distilled water and the mixture was homogenized with a Polytron-like mixer. This was added to Casein mixture slowly (with continuation of mixing in the homogenizer).

(d) $CaCO_3 \cdot 2H_2O$ (10 g) and Ca-citrate (4.8 g) were dissolved in 100 ml of distilled water and, after autoclaving, the solution was added to Casein mixture slowly.

(e) $Na_2HPO_4$ (3.2 g) and $KH_2PO_4$ (0.32 g) were dissolved in 50 ml of distilled water and, after sterilization with an autoclave, the solution was added to Casein mixture.

(f) After sterilization with an autoclave, a lactose aqueous solution (obtained by dissolving 75.64 g of lactose in 220 ml of distilled water) was added to Casein mixture slowly.

(g) $FeSO_4 \cdot 7H_2O$ (1.92 g) and $Citrate-H_2O$ (0.04 g) were dissolved in 20 ml of distilled water. 10 ml of the resulting solution, $ZnSO_4 \cdot 7H_2O$ (1.2 g), $CuSO_4 \cdot 5H_2O$ (0.3 g), and $MnSO_4 \cdot 5H_2O$ (0.05 g) were dissolved in 25 ml of distilled water. 5 ml of the resulting solution, NaF (0.031 g), and KI (0.05 g) were dissolved in 25 ml of distilled water. 5 ml of the resulting solution was added to Casein mixture. This procedure was conducted with constant stirring after sterilization with Millipore Filtration (0.45 μm).

(h) Whey protein isolate (160 g) and Whey protein hydrolysate (200 g) sterilized by gamma irradiation (30 KGy) were dissolved in 1000 ml of sterilization distilled water and this solution was added to Casein mixture that was cooled to 40° C. or lower with stirring.

(i) Carnitine (0.32 g), picolinic acid (0.16 g), ethanolamine (0.272 g), and taurine (1.2 g) were dissolved in 20 ml of distilled water. 10 ml of the resulting solution was added to Casein mixture.

(j) In a neutralized solution (neutralized to pH 7.0 with 1N NaOH) of choline dihydrogen citrate (5.88 g) dissolved in 73.5 ml of distilled water (in water bath at 65° C.), a water-soluble vitamin mixture (cyanocobalamin (0.0476 mg), biotin (0.72 mg), folic acid (3.16 mg), thiamine hydrochloride (35.24 mg), pyridoxine hydrochloride (50.0 mg), riboflavin sodium phosphate (56.6 mg), calcium pantothenate (105.72 mg), p-aminobenzoic acid (176.16 mg), nicotinic acid (199.52 mg), sodium ascorbate (2.696 g), and 4-inositol (1.989 g)) was dissolved. 70 ml of the resulting solution was added to Casein mixture.

(k) Fat-solubility vitamins (a mixture comprising vitamin $K_3$ (79.3 mg), vitamin E: α-tocopherol (93.8 mg), and vitamins A and D) and 6 edible oils (palm oil (191.5 g), coconut oil (159.6 g), corn oil (63.84 g), medium-chain triglyceride oil (95.76 g), soybean oil (127.68 g), and cholesterol (1.6 g)) were sterilized in a boiling water bath for 30 minutes. This oily solution was cooled to 40 to 50° C. and then added to Casein mixture with stirring.

(l) After the homogenization, the artificial milk was sterilely dispensed into 50 ml sterilized polypropylene bottles and stored at −80° C. The frozen artificial milk was sterilized by gamma irradiation (30 KGy) and stored at −80° C.

The day of birth was set at day 0 after birth and murine neonates breast-fed from day 0 to day 2 after birth were separated from the parents and lactated with artificial milk by oral administration using a milk container once in 3 hours from day 2 after birth. During the artificial lactation period, the amount of lactation and the body weight were measured successively. After 8 days of artificial lactation to day 10, the mice were euthanized by excess inhalation of diethyl ether and autopsied to extract the thymus.

The extracted thymus was weighed and transferred into a laboratory dish filled with phosphate-buffered balanced salt solution (PBBS) supplemented with 0.1% bovine serum albumin (BSA). After slicing the tissue with scissors to some extent in the laboratory dish, the extracted thymus was ground with a frost part of a microscope slide and the suspension was filtered through a 42K mesh using a pipette and transferred into a conical tube. The filtrate was centrifuged for 5 minutes at 800 rpm and the supernatant was removed by decantation. An ammonium chloride solution (Tris-buffered ammonium chloride: ACTB) for removing erythrocytes was added to the remaining thymocytes and mixed by pipetting and the suspension was left stand at room temperature for 5 minutes for the hemolysis. Subsequently, cold PBBS was added and the suspension was centrifuged for 5 minutes at 800 rpm and the supernatant was removed by decantation. Cold PBBS was added for washing and the operations of the centrifugation for 5 minutes at 800 rpm and the removal of supernatant were repeated twice. Then, the suspension was transferred to an Eppendorf tube. The obtained solution was diluted as appropriate and the total number of cells and the number of lymphocytes were counted to compare the control group and the CCL25 administered group. All statistical processing of experimental results was conducted using t-test.

Figure 4:
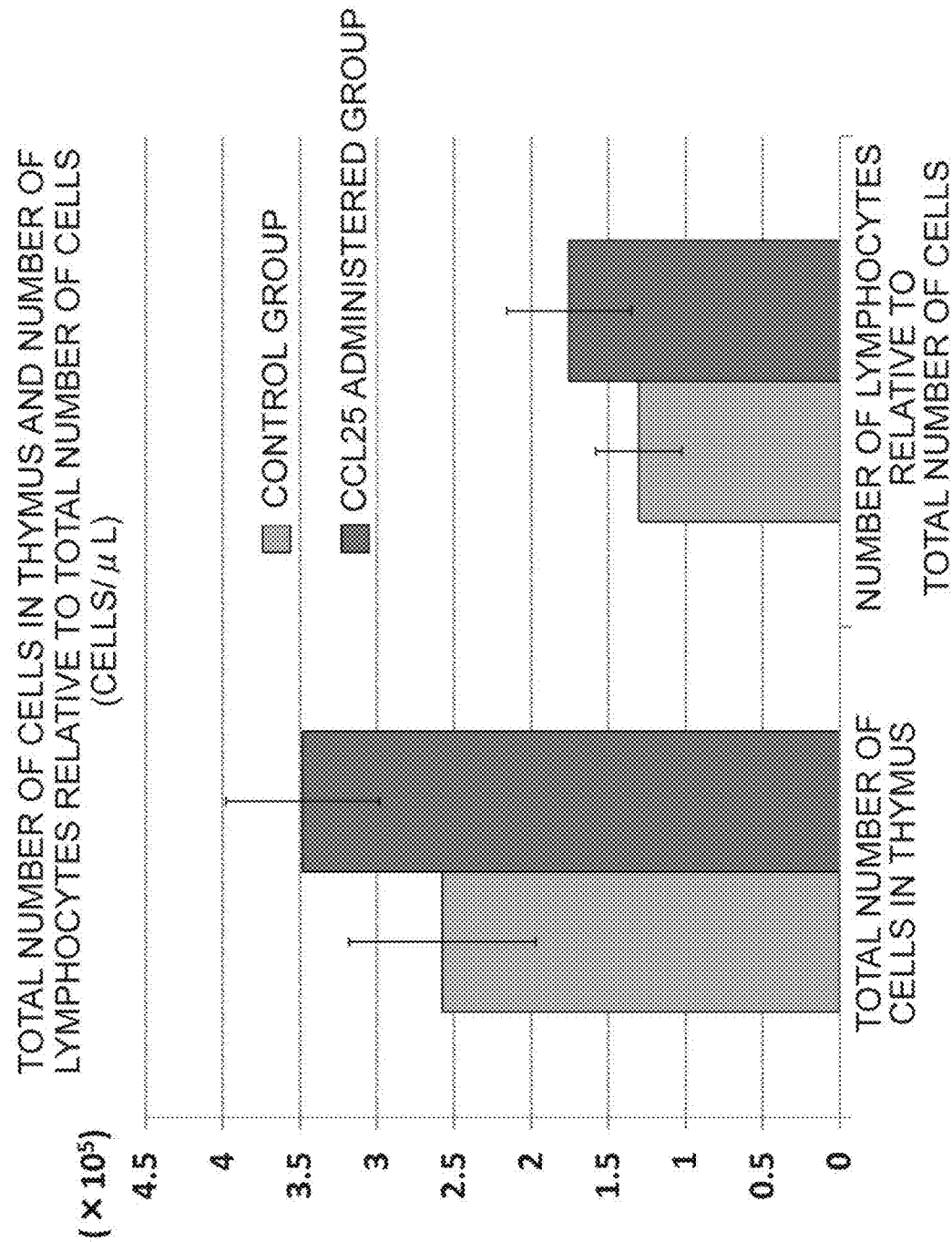
FIG. 4 is a graph comparing the total number of cells in the thymus and the number of lymphocytes relative to the total number of cells in the CCL25 administered group and the control group.

There was the tendency that the total number of cells in the thymus in the CCL25 administered group was higher than that in the control group. Moreover, the number of lymphocytes relative to the total number of cells tended to be higher in the CCL25 administered group than that in the control group (FIG. 4).

From the foregoing results, the promoting effects of the addition of CCL25 on the immune function development and the growth were confirmed.

The invention claimed is:

1. A method for promoting immune function development in a subject, comprising administering Chemokine (C-C motif) ligand 25 (CCL25) protein in a composition to a subject in need thereof, wherein the CCL25 protein is orally administered; with the proviso that the composition is not milk itself obtained from the mother's body.

2. The method according to claim 1, wherein the subject is an infant.

3. A method for promoting growth of a subject, comprising administering Chemokine (C-C motif) ligand 25 (CCL25) in a composition to a subject in need thereof; with the proviso that the composition is not milk itself obtained from the mother's body.

4. The method according to 3, wherein the subject is an infant.

5. The method according to 4, wherein the CCL25 is orally administered.

6. The method according to 3, wherein the CCL25 is orally administered.

* * * * *